(12) United States Patent
Jia et al.

(10) Patent No.: US 12,247,971 B2
(45) Date of Patent: Mar. 11, 2025

(54) METHOD AND DEVICE FOR EVALUATING AGING STATE OF SILICONE RUBBER COMPOSITE INSULATOR

(71) Applicants: State Grid Hebei Electric Power Co., Ltd. Research Institute, Hebei (CN); State Grid Corporation of China, Beijing (CN); State Grid Hebei Energy Technology Service Co., Ltd., Hebei (CN); HEBEI SILICON VALLEY CHEMICAL CO., LTD., Hebei (CN); ZIBO QIANHENG AUTOMATION ENGINEERING CO., LTD., Shandong (CN)

(72) Inventors: Boyan Jia, Hebei (CN); Jie Liu, Hebei (CN); Yanwei Xia, Hebei (CN); Xianhai Pang, Hebei (CN); Yuhao Zhao, Hebei (CN); Shilin Li, Hebei (CN); Liqiang Song, Hebei (CN); Xiangxia Liu, Shandong (CN)

(73) Assignees: State Grid Hebei Electric Power Co., Ltd. Research Institute, Shijiazhuang (CN); State Grid Corporation of China, Beijing (CN); State Grid Hebei Energy Technology Service Co., Ltd., Shijiazhuang (CN); HEBEI SILICON VALLEY CHEMICAL CO., LTD., Handan (CN); ZIBO QIANHENG AUTOMATION ENGINEERING CO., LTD., Zibo (CN)

( * ) Notice: Subject to any disclaimer, the term of this patent is extended or adjusted under 35 U.S.C. 154(b) by 0 days.

(21) Appl. No.: 17/789,534

(22) PCT Filed: Dec. 10, 2021

(86) PCT No.: PCT/CN2021/137084
§ 371 (c)(1),
(2) Date: Jun. 28, 2022

(87) PCT Pub. No.: WO2023/102893
PCT Pub. Date: Jun. 15, 2023

(65) Prior Publication Data
US 2024/0192191 A1    Jun. 13, 2024

(30) Foreign Application Priority Data
Dec. 8, 2021    (CN) .......................... 202111493264.1

(51) Int. Cl.
*G01N 17/00*    (2006.01)
*G01N 3/20*    (2006.01)
(Continued)

(52) U.S. Cl.
CPC ............ *G01N 33/445* (2013.01); *G01N 3/20* (2013.01); *G01N 3/40* (2013.01); *G01N 21/31* (2013.01)

(58) Field of Classification Search
CPC .......... G01N 33/445; G01N 3/20; G01N 3/40; G01N 21/31; G01N 3/44; G01N 13/00;
(Continued)

(56) References Cited

FOREIGN PATENT DOCUMENTS

| CN | 105403777 A | 3/2016 |
|---|---|---|
| CN | 108872059 A | 11/2018 |

(Continued)

*Primary Examiner* — Mohamed Charioui
*Assistant Examiner* — Christine Y Liao (57) ABSTRACT

A method for evaluating an aging state of a silicone rubber composite insulator includes: step 1: collecting samples from the silicone rubber composite insulator, and subjecting samples in a surface layer and a center layer successively to hydrophobicity, flexing resistance, hardness, color, and absorbance tests; step 2: determining relevant data of the samples in a natural evolution process according to the tests in step 1; step 3: subjecting the samples to thermo-oxidative (Continued)

aging; and after the thermo-oxidative aging is completed, subjecting the samples to a hardness test of artificial accelerated evolution, and calculating position coordinates ($F_1$, $F_2$) of the samples in an aging space; and step 4: classifying the samples in advance and solving an aging state centroid of each classified population, calculating a minimum aging distance based on the position coordinates in step 3, and evaluating the aging state of the silicone rubber composite insulator.

18 Claims, 5 Drawing Sheets

(51) Int. Cl.
  *G01N 3/40* (2006.01)
  *G01N 21/31* (2006.01)
  *G01N 33/44* (2006.01)
(58) Field of Classification Search
  CPC ... G01N 2203/0023; G01N 2203/0076; G01R 31/1263; G01R 31/1218
  See application file for complete search history.

(56) References Cited

FOREIGN PATENT DOCUMENTS

| | | | |
|---|---|---|---|
| CN | 105403777 B | * | 8/2019 |
| CN | 112229813 A | | 1/2021 |
| CN | 114119533 A | * | 3/2022 |

* cited by examiner

METHOD AND DEVICE FOR EVALUATING AGING STATE OF SILICONE RUBBER COMPOSITE INSULATOR

TECHNICAL FIELD

The present disclosure relates to the technical field of high-voltage insulation, and specifically to a method and device for evaluating an aging state of a silicone rubber composite insulator.

BACKGROUND

Since the large-scale pollution flashover accident at the end of the last century and the beginning of this century in China, silicone rubber composite insulators have been widely favored by electric power enterprises due to their excellent anti-pollution flashover performance. So far, the number of composite insulators in operation in China has exceeded 10 million. However, silicone rubber materials are a group of organic polymer materials, and during an operation process, an operation state thereof will inevitably deteriorate (namely, aging) due to the combined action of electric field, pollution, ultraviolet (UV) ray, high temperature, moisture, and other factors.

For this reason, research institutions and scholars in and outside China have conducted a lot of research on the aging characteristics of silicone rubber materials, and put forward a large number of test methods such as hardness, hydrophobicity, tracking resistance, molecular group content, and activation energy tests. However, factors affecting the aging of running composite insulators are complex and diverse, and the aging of silicone rubber materials involves various chemical and physical reactions such as condensation, cracking, cross-linking, hydrolysis, and small-molecule hydrophobic substance migration, which makes the aging properties of silicone rubber materials also show a trend of non-monotonic change. For example, there is some degree of inconsistency between a single aging index (such as hydrophobicity, microscopic morphology, molecular group content, and element content) and a true aging state of a silicone rubber material. This inconsistency exacerbates phenomena such as "over repair" and "out of repair" for composite insulators, which increases an investment on the operation and maintenance of a power grid, and may even cause a sudden increase in the pollution flashover risk of a power grid.

In addition, there are technical means in the prior art that adopt multiple methods to simultaneously evaluate the aging characteristics of silicone rubber materials. For example, in Chinese patent CN112229813A, a Fourier transform infrared spectroscopy (FTIR) analysis method, a thermally stimulated current (TSC) analysis method, and a scanning electron microscopy (SEM) analysis method are used for test to obtain an aging state of a composite insulator.

However, although the combined detection method used in the prior art can determine an aging state of a silicone rubber composite insulator from various perspectives, a high overall cost is required, and a determination result still cannot fully meet the requirements of aging state evaluation. Moreover, the method in the prior art can only evaluate a current aging state of a silicone rubber composite insulator, but cannot reasonably evaluate an aging risk of a silicone rubber composite insulator in continuous use. In addition, due to the diversity of evaluation means, there is a contradiction between aging evaluation accuracy and evaluation time of a silicone rubber composite insulator, and the improvement of evaluation accuracy must come at the cost of evaluation time extension.

In view of the above problems, a new method for evaluating an aging state of a silicone rubber composite insulator is urgently needed.

SUMMARY

In order to solve the deficiencies in the prior art, the present disclosure is intended to provide a method for evaluating an aging state of a silicone rubber composite insulator, where samples of the silicone rubber composite insulator are subjected to hydrophobicity, flexing resistance, hardness, color, and absorbance tests to obtain an overall aging state of the silicone rubber composite insulator.

The present disclosure adopts the following technical solutions. In a first aspect of the present disclosure, a method for evaluating an aging state of a silicone rubber composite insulator is provided, including the following steps: step 1: collecting samples from the silicone rubber composite insulator, subjecting samples in a surface layer successively to hydrophobicity, flexing resistance, hardness, color, and absorbance tests, and subjecting samples in a center layer successively to hardness, color, and absorbance tests; step 2: determining an average static contact angle, a flexing resistance index, a hardness difference, a color difference, and an absorbance rise rate of the samples during a natural evolution process according to the tests in step 1; step 3: subjecting the samples to thermo-oxidative aging; and after the thermo-oxidative aging is completed, subjecting the samples to a hardness test of artificial accelerated evolution, and calculating position coordinates $(F_1, F_2)$ of the samples in an aging space; and step 4: classifying the samples in advance and solving an aging state centroid of each classified population, calculating a minimum aging distance based on the position coordinates in step 3, and evaluating the aging state of the silicone rubber composite insulator based on the minimum aging distance.

Preferably, the step of collecting samples from the silicone rubber composite insulator may include: step 1.1: randomly collecting a whole umbrella skirt $S_{zp}$ of a second umbrella or a third umbrella of a high-voltage end from the silicone rubber composite insulator; step 1.2: collecting samples $A_w$, $B_w$, $C_w$, and $D_w$ respectively from four positions a, b, c, and d on an upper surface of the whole umbrella skirt $S_{zp}$; and step 1.3: collecting samples $A_n$, $B_n$, $C_n$, and $D_n$ respectively from four positions a, b, c, and d in a split layer of the whole umbrella skirt $A_n$; where a connecting line ab is perpendicular to a connecting line cd, and an intersection point of the two is located at a pivot of the whole umbrella skirt; and distances of the four points a, b, c, and d to the pivot of the whole umbrella skirt are equal.

Preferably, the samples $A_w$, $B_w$, $C_w$, and $D_w$ may be each subjected to a hydrophobicity test, and static contact angles of surfaces of the samples may be recorded as $CAV_{A_w}$, $CAV_{B_w}$, $CAV_{C_w}$, and $CAV_{D_w}$; and an average static contact angle $\Delta CAV = CAV_{i_w}/4$ of the samples may be calculated based on the static contact angles of the surfaces of the samples, where i=A, B, C, or D.

Preferably, the subjecting the samples to a flexing resistance test may specifically include: folding an edge of the sample $S_{zp}$ at 180°, and determining a flexing resistance index $C_{dz}$ based on a crack state at a crease position, where $$C_{dz} = \begin{cases} 0, & \text{There are cracks} \geq 2 \text{ mm.} \\ 1, & \text{There are cracks} \leq 2 \text{ mm.} \\ 2, & \text{There is no crack} \end{cases}$$

Preferably, the subjecting the samples to a hardness test in step 1 may further include: subjecting the samples $A_w$, $B_w$, $C_w$, $D_w$, $A_n$, $B_n$, $C_n$, and $D_n$ to a Shore hardness test to obtain Shore hardness values $\text{Shore}_{iw}$ and $\text{Shore}_{in}$ of a sample at each position, where i=A, B, C, or D; calculating a Shore hardness difference $\text{Shore}_i = \text{Shore}_{iw} - \text{Shore}_{in}$ of a sample at each position; and calculating a natural evolution difference $\Delta H_{shore} = \Sigma(\text{Shore}_{iw} - \text{Shore}_{in})/4$ in Shore hardness of the samples at the four positions.

Preferably, the subjecting the samples to a color test in step 1 may further include: subjecting the samples $A_w$, $B_w$, $C_w$, $D_w$, $A_n$, $B_n$, $C_n$, and $D_n$ to a lightness test to obtain lightness values $L_{iw}$ and $L_{in}$ of a sample at each position in a color space L*a*b, where i=A, B, C, or D; calculating a lightness difference $L_i = L_{iw} - L_{in}$ of a sample at each position; and calculating a natural evolution difference $\Delta L = \Sigma(L_{iw} - L_{in})/4$ in lightness of the samples at the four positions.

Preferably, the samples $A_w$, $B_w$, $C_w$, $D_w$, $A_n$, $B_n$, $C_n$, and $D_n$ may be subjected to an absorbance test, and absorbance ratios $R_{iw}$ and $R_{in}$ of a sample at each position may be recorded, where i=A, B, C, or D; an absorbance rise rate $$IR_i = \frac{(R_{iw} - R_{in})}{R_{in}} * 100\%$$

of a sample at each position may be calculated; and a natural evolution $\Delta IR = \Sigma IR_i/4$ of the absorbance rise rates of the samples at the four positions may be calculated.

Preferably, the absorbance ratios $R_{iw}$ and $R_{in}$ of the sample at each position may be determined as follows: determining an absorbance peak of the sample at a wavelength corresponding to siloxy and an absorbance peak at a wavelength corresponding to silyl; and calculating a ratio of the two peaks to obtain the absorbance ratios $R_{iw}$ and $R_{in}$.

Preferably, a method of the thermo-oxidative aging in step 2 may include: subjecting samples $A_w$, $B_w$, $C_w$, and $D_w$ simultaneously to thermo-oxidative aging at 290° C. for 12 h.

Preferably, the subjecting the samples to a hardness test in step 3 may be conducted by a method the same as the method of the subjecting the samples to a hardness test in step 1 to obtain a Shore hardness value $\text{Shore}_{iwlh}$ of each sample, where i=A, B, C, or D;

a hardness difference $\text{Shore}_{ilh} = \text{Shore}_{iwlh} - \text{Shore}_{iw}$ may be calculated for each sample after the thermo-oxidative aging; and an artificial accelerated evolution difference $\Delta H_{lh} = \Sigma \text{Shore}_{ilh}/4$ in Shore hardness of the four samples may be calculated.

Preferably, in a laboratory evaluation process, the position coordinates $(F_1, F_2)$ of the samples in the aging space may be calculated according to the following formula:

$F_1 = \alpha_1 \Delta H_{lh} + \alpha_2 \Delta CAV + \alpha_3 \Delta H_{shore} + \alpha_4 \Delta L + \alpha_5 \Delta IR + \alpha_6$ $F_2 = \beta_1 \Delta H_{lh} + \beta_2 \Delta CAV + \beta_3 \Delta H_{shore} + \beta_4 \Delta L + \beta_5 \Delta IR + \beta_6$, where a projection matrix $$C = \begin{bmatrix} \alpha_1 & \alpha_2 & \alpha_3 & \alpha_4 & \alpha_5 & \alpha_6 \\ \beta_1 & \beta_2 & \beta_3 & \beta_4 & \beta_5 & \beta_6 \end{bmatrix}$$

composed of coefficients in the position coordinate calculation formula is calculated in advance based on Fisher discriminant analysis (FDA).

Preferably, a calculation process of the projection matrix C may include: step 3.1: subjecting a preset sample group to overall classification to divide the preset sample group into n populations according to an aging degree; step 3.2: calculating an intra-population sum of squares (SS) of all samples in each population, and calculating an inter-population SS of multiple populations; and step 3.3: calculating the matrix C using an objective function that makes the intra-population SS minimum and the inter-population SS maximum after projection.

Preferably, in an on-site evaluation process, the position coordinates of the samples in the aging space may be calculated only based on the natural evolution difference in lightness $\Delta L$ and the flexing resistance index $C_{dz}$.

Preferably, an aging state centroid of samples in each classified population may be calculated, a distance between each preset centroid and the position coordinates $(F_1, F_2)$ may be calculated, and a minimum distance value may be adopted as the minimum aging distance minL; and multiple classified populations may be determined, and when a discrimination index between any two classified populations is less than a set threshold, the number of classified populations may be reduced and then the aging state centroid may be recalculated.

Preferably, the number of classified populations of samples may be 3, and an unaging state centroid $(F_1\ _{unaging}, F_2\ _{unaging})$, a slightly-aging state centroid $(F_1\ _{slightly-aging}, F_2\ _{slightly-aging})$, and a severely-aging state centroid $(F_1\ _{severely-aging}, F_2\ _{severely-aging})$ of the samples may be calculated; and in a laboratory evaluation process, distances of the unaging state centroid, the slightly-aging state centroid, and the severely-aging state centroid to the coordinate position may be each calculated.

Preferably, in an on-site evaluation process, populations may be divided into non-aging populations and aging populations, and distances of a non-aging state centroid and an aging state centroid to the coordinate position may be each calculated.

In a second aspect of the present disclosure, a device for evaluating an aging state of a silicone rubber composite insulator is provided, where the device integrates a hydrophobicity detection module, a Shore hardness tester, a lightness detection module, an FTIR detection module, a wireless transmission module, and an evaluation module, where the hydrophobicity detection module, the Shore hardness tester, the lightness detection module, and the FTIR detection module are configured to test samples by the method in the first aspect of the present disclosure; the wireless transmission module is configured to output test results of the hydrophobicity detection module, the Shore hardness tester, the lightness detection module, and the FTIR detection module to the evaluation module in real time; and the evaluation module is configured to evaluate the test results and display the aging state of the silicone rubber composite insulator.

Preferably, the device may further include a selection module configured to select a calculation method of position coordinates of the samples in an aging space.

The present disclosure has the following beneficial effects: Compared with the prior art, the method for evaluating an aging state of a silicone rubber composite insulator provided in the present disclosure can determine an overall aging state of the silicone rubber composite insulator by subjecting samples of the silicone rubber composite insulator to hydrophobicity, flexing resistance, hardness, color, and absorbance tests. In addition, in the present disclosure, the samples can be subjected to thermo-oxidative aging, and after the thermo-oxidative aging is completed, aging test results of the silicone rubber composite insulator are further determined, such that the future aging performance of the silicone rubber composite insulator product can be accurately predicted, and thus operation and maintenance personnel of a power grid can reasonably choose the time to replace the composite insulator product.

The present disclosure also has the following beneficial effects:

1. In the present disclosure, multiple samples can be collected from different positions of the silicone rubber composite insulator, and the samples collected from different positions of the composite insulator can be subjected to comparative analysis, such that the aging state of the composite insulator can be accurately inferred according to aging degree differences of the sample surfaces and the sample interiors respectively. Moreover, the method of collecting samples from multiple different positions for test reduces evaluation errors caused by uneven aging due to differences of light, contamination, and the like among various positions of a silicone rubber composite insulator in use, making an evaluation result more accurate.

2. Since indexes such as natural evolution of aging performance and artificial accelerated evolution of aging performance are introduced in the method of the present disclosure, the aging characteristics of a silicone rubber material in the whole life cycle can be reasonably and accurately characterized, which reduces the uncertainty of evaluation caused by aging performance fluctuations due to the diversity characteristic of aging reactions.

3. The method of the present disclosure adopts multiple manners to calculate aging position coordinates, reasonably sets multiple aging centroids, and accurately determines an aging evaluation result of a silicone rubber composite insulator through a mathematical approach. In the present disclosure, two different methods are used to calculate the position coordinates. A calculation process of a first method is comprehensive and accurate, but is time-consuming. A second method is simple and easy to operate. In the case of high timeliness requirements, the second method can be selected for test. In addition, since the two methods are conducted at the same time, the second method can be verified based on an evaluation result of the first method in an appropriate case, such that the accuracy of the second method can be reasonably improved by an optimization coefficient or the like, which ensures that the requirements of both evaluation accuracy and evaluation time consumption can be met.

4. The device of the present disclosure integrates an evaluation module and a wireless transmission module, and realizes automatic recording and calculation of test results through the Internet of Things (IoT) method, which significantly reduces the workload of test personnel, improves the work efficiency, and reduces operation errors in a test process. The device of the present disclosure integrates corresponding evaluation and calculation software, and thus can automatically call a detection result for data processing, which is convenient and easy to implement, and improves the test efficiency.

DETAILED DESCRIPTION

The prevent disclosure is further described below with reference to the accompanying drawings. The following embodiments are only used for describing the technical solutions of the present disclosure more clearly, and are not intended to limit the protection scope of the present disclosure.

Figure 1:
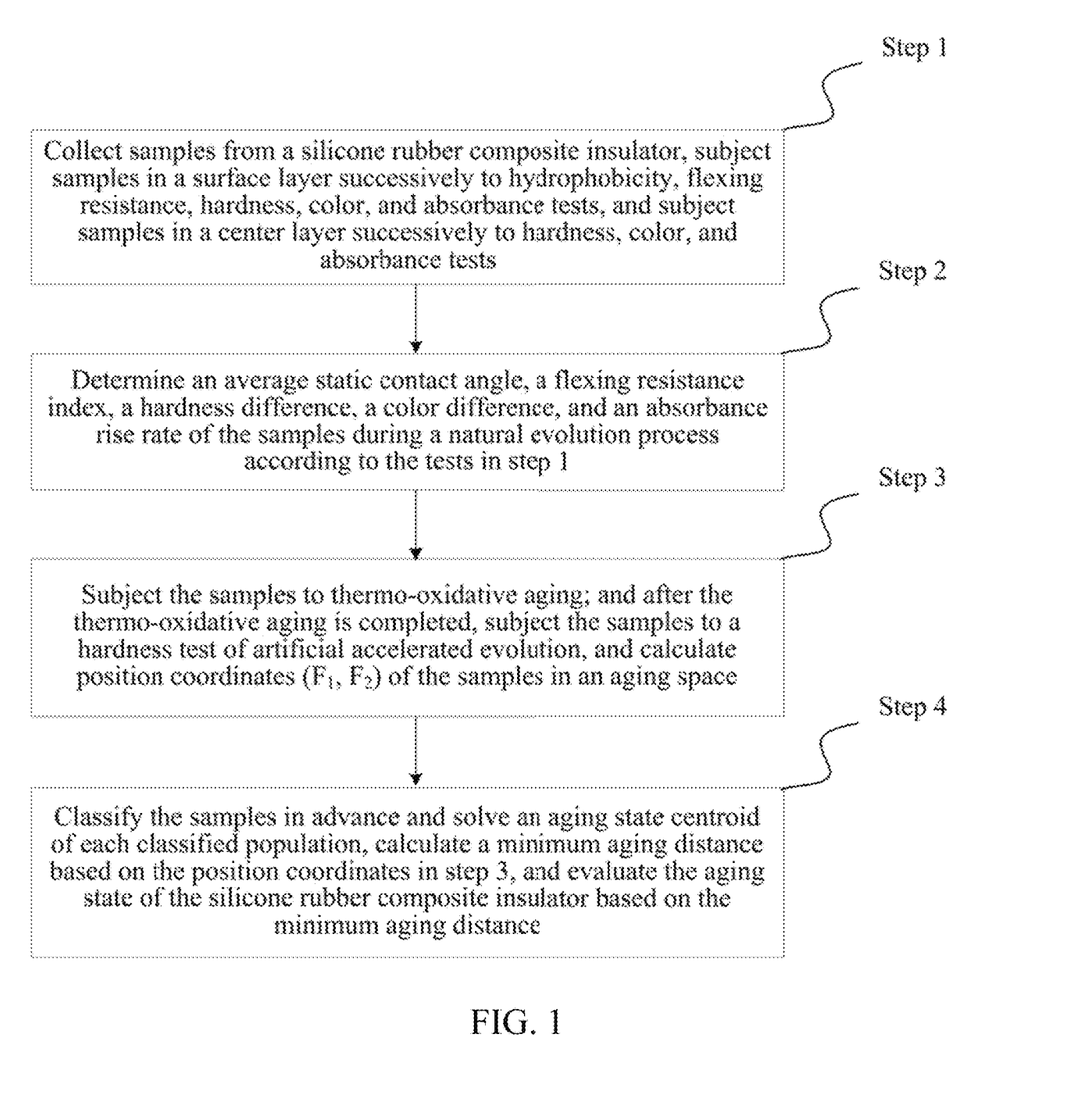
FIG. 1 is a flow chart of the method for evaluating an aging state of a silicone rubber composite insulator according to the present disclosure.

FIG. 1 is a flow chart of the method for evaluating an aging state of a silicone rubber composite insulator according to the present disclosure. As shown in FIG. 1, according to a first aspect of the present disclosure, a method for evaluating an aging state of a silicone rubber composite insulator is provided, including the following steps:

Step 1: Samples are collected from the silicone rubber composite insulator, samples in a surface layer are subjected successively to hydrophobicity, flexing resistance, hardness, color, and absorbance tests, and samples in a center layer are subjected successively to hardness, color, and absorbance tests.

In the present disclosure, a silicone rubber insulator to be tested can be selected first, and multiple samples on the insulator can be collected in steps.

Preferably, the step of collecting samples from the silicone rubber composite insulator may include: step 1.1: randomly collecting a whole umbrella skirt $S_{zp}$ of a second umbrella or a third umbrella of a high-voltage end from the silicone rubber composite insulator; step 1.2: collecting samples $A_w$, $B_w$, $C_w$, and $D_w$ respectively from four positions a, b, c, and d on an upper surface of the whole umbrella skirt $S_{zp}$; and step 1.3: collecting samples $A_n$, $B_n$, $C_n$, and $D_n$ respectively from four positions a, b, c, and d in a split layer of the whole umbrella skirt $S_{zp}$; where a connecting line ab is perpendicular to a connecting line cd, and an intersection point of the two is located at a pivot of the whole umbrella skirt; and distances of the four points a, b, c, and d to the pivot of the whole umbrella skirt are equal.

It should be appreciated that, in the present disclosure, in order to obtain an aging state of a silicone rubber composite insulator, a corresponding umbrella skirt of a part that is most easily aged can be selected from the composite insulator, for example, in a highest direction at the vertical position of the mounting position of the composite insulator, that is, the whole umbrella skirt of the second umbrella to the third umbrella at the high-voltage end. Or, a piece of umbrella skirt can be randomly selected. Generally, the composite insulators in the prior art include multiple conventional umbrella skirts and multiple small barbed sawteeth, and the appearance of such burrs and sawtooth structures in some composite insulators is similar to the appearance of umbrella skirts, but these burrs and sawtooth structures are not the target of random sampling in the present disclosure. Further, some insulators include multiple conventional umbrella skirts of different sizes, and the plurality of umbrella skirts of different sizes are arranged at a specific interval. In the present disclosure, for adequate sampling and test of the samples, the whole umbrella skirt of the second umbrella to the third umbrella at the high-voltage end is acquired from an umbrella with the largest size.

The whole umbrella skirt is recorded as a sample $S_{zp}$, and then multiple samples can be collected from the umbrella skirt. Some of the plurality of samples can be located on a surface of the umbrella skirt that is in direct contact with air, light, moisture, and the like for a long time, and the remaining can be located inside the umbrella skirt.

By this selection method, aging indexes on the surface of and inside the umbrella skirt can be obtained multiple times, and the two types pf aging indexes can be compared to obtain a difference between the two types pf aging indexes from a spatial perspective, thereby accurately analyzing the overall aging performance; and according to a distance between an internal sample and a surface of the silicone rubber material, a time period for which the interior of the silicone rubber composite insulator with a specified volume or thickness has been affected by aging can be predicted.

In the present disclosure, in order to prevent single-sided illumination or local fouling from greatly affecting the measurement accuracy, with a pivot of the composite insulator in the present disclosure as a coordinate origin, four positions are selected in four directions at angles of 0°, 90°, 180°, and 270° respectively with an axial direction for sampling, and the four positions are basically at the same distance from the coordinate origin.

After samples are collected, relevant tests can be conducted to evaluate the aging state of the silicone rubber composite insulator. In the present disclosure, the hydrophobicity, flexing resistance, hardness, color, and absorbance tests are conducted in sequence. According to the methods in the prior art, some test contents can be appropriately added or reduced based actual conditions or needs. Since multiple test results in the present disclosure are evaluated and calculated through a weight, according to actual test results and accuracy, the types of tests can be increased or decreased reasonably or a weight used for test results in an evaluation process can be optimized.

Step 2: An average static contact angle, flexing resistance, a hardness difference, a color difference, and an absorbance rise rate of the samples during a natural evolution process are determined according to the tests in step 1.

In the present disclosure, multiple test results are obtained based on the multiple tests in step 1. It should be noted that, before the subsequent tests, it is necessary to ensure that all cut surfaces of the samples are smooth and clean. Moreover, after other samples are collected from the sample $S_{zp}$, the relative integrity of the sample $S_{zp}$ should also be ensured.

Preferably, the samples $A_w$, $B_w$, $C_w$, and $D_w$ may be each subjected to a hydrophobicity test, and static contact angles of surfaces of the samples may be recorded as $CAV_{A_w}$, $CAV_{B_w}$, $CAV_{C_w}$, and $CAV_{D_w}$; and an average static contact angle $\overline{CAV} = \Sigma CAV_{i_w}/4$ of the samples may be calculated based on the static contact angles of the surfaces of the samples, where i=A, B, C, or D.

It should be appreciated that, in the present disclosure, the four samples can be each tested to obtain the hydrophobicity of the aged silicone rubber material. In the present disclosure, only the four samples on an upper surface of the umbrella skirt are subjected to the hydrophobicity test. This is because the four samples inside have a low aging degree, and thus show basically the same hydrophobicity as an ordinary silicone rubber material just manufactured. Therefore, the test on the four samples inside is omitted in the present disclosure.

In addition, the static contact angle of each sample ($CAV_{A_w}$, $CAV_{B_w}$, $CAV_{C_w}$, and $CAV_{D_w}$) can be obtained by measuring a corresponding sample 5 times and taking an average value, which is expressed in a unit of °. Preferably, the subjecting the samples to a flexing resistance test may specifically include: folding an edge of the sample $S_{zp}$ at 180°, and determining a flexing resistance index $C_{dz}$ based on a crack state at a crease position, where $$C_{dz} = \begin{cases} 0, & \text{There are cracks} \geq 2 \text{ mm.} \\ 1, & \text{There are cracks} \leq 2 \text{ mm.} \\ 2, & \text{There is no crack} \end{cases}$$

It should be appreciated that a specific process of the flexing resistance test in the present disclosure can be conducted manually, and in a process of determining the flexing resistance index, it is not necessary to generate the flexing resistance index strictly according to a size or degree of the crack, and generally, this process can be based on empirical determination.

Preferably, the subjecting the samples to a hardness test in step 1 may further include: subjecting the samples $A_w$, $B_w$, $C_w$, $D_w$, $A_n$, $B_n$, $C_n$, and $D_n$ to a Shore hardness test to obtain Shore hardness values $Shore_{iw}$ and $Shore_{in}$ of a sample at each position, where i=A, B, C, or D; calculating a Shore hardness difference $Shore_i = Shore_{iw} - Shore_{in}$ of a sample at each position; and calculating a natural evolution difference $\Delta H_{shore} = \Sigma(Shore_{iw} - Shore_{in})/4$ in Shore hardness of the samples at the four positions.

In the present disclosure, the Shore hardness index can be used to test the hardness of the aged silicone rubber material. Because this index is accurate for the detection of aging degree (or in other words, this index shows a relatively high confidence level for aging determination), a coefficient thereof is set to be large in the subsequent method of the present disclosure.

In the present disclosure, a handheld A-type Shore hardness tester can be used to test an outer surface of the sample, and the index is measured in the unit of HA.

Preferably, the subjecting the samples to a color test in step 1 may further include: subjecting the samples $A_w$, $B_w$, $C_w$, $D_w$, $A_n$, $B_n$, $C_n$, and $D_n$ to a lightness test to obtain lightness values $L_{iw}$ and $L_{in}$ of a sample at each position in a color space L*a*b, where i=A, B, C, or D; calculating a lightness difference $L_i = L_{iw} - L_{in}$ of a sample at each position; and calculating a natural evolution difference $\Delta L = \Sigma(L_{iw} - L_{in})/4$ in lightness of the samples at the four positions.

As an aging degree increases, a color of the silicone rubber material will change to some extent compared with its original color, for example, the lightness is decreased. Therefore, lightness differences among samples at different positions can be comprehensively considered, and a natural evolution can be obtained through averaging.

Preferably, the samples $A_w$, $B_w$, $C_w$, $D_w$, $A_n$, $B_n$, $C_n$, and $D_n$ may be subjected to an absorbance test, and absorbance ratios $R_{iw}$ and $R_{in}$ of a sample at each position may be recorded, where i=A, B, C, or D; an absorbance rise rate $$IR_i = \frac{(R_{iw} - R_{in})}{R_{in}} * 100\%$$

of a sample at each position may be calculated; and a natural evolution $\Delta IR=\Sigma IR_i/4$ of the absorbance rise rates of the samples at the four positions may be calculated.

It should be appreciated that, according to a chemical composition of the silicone rubber material, the main chemical bonds (silicon-oxygen bond and silicon-methyl bond) in the silicone rubber material will cause a large amount of absorption in an infrared spectrum. Therefore, an infrared spectrometer can be used to generate a large amount of infrared rays, and a spectral line generated after the absorption of the silicone rubber material is acquired. Wavelength or frequency positions corresponding to the silicon-oxygen bond and silicon-methyl bond are found in the spectral line to obtain spectra generated from the absorption of the two chemical bonds. On these two specific spectra, absorbance indexes of the two different chemical bonds can be obtained according to peak values of absorption spectra, and the two absorbance indexes can be divided to obtain an actual proportional relationship between the two chemical bonds in the silicone rubber material, that is, an actual composition of the silicone rubber material can be determined, or an estimated proportion of a corresponding component in the silicone rubber material can be determined.

Preferably, the absorbance ratios $R_{iw}$ and $R_{in}$ of the sample at each position may be determined as follows: determining an absorbance peak of the sample at a wavelength corresponding to oxygen-silicon bond and an absorbance peak at a wavelength corresponding to silicon-methyl bond; and calculating a ratio of the two peaks to obtain the absorbance ratios $R_{iw}$ and $R_{in}$.

In addition, in the present disclosure, a density of the sample can also be determined by the drainage method, with g/cm² as a measuring unit. Moreover, a cross-linking density of the sample can be determined by the equilibrium swelling method, in a unit of mol/m³.

Since the actual composition of the silicone rubber material has been determined, a degree of chemical reactions in the silicone rubber material caused by aging can be determined, and then an aging degree can be determined.

Preferably, a method of the thermo-oxidative aging in step 2 may include: subjecting samples $A_w$, $B_w$, $C_w$, and $D_w$ simultaneously to thermo-oxidative aging at 290° C. for 12 h.

In the method of the present disclosure, the thermo-oxidative aging can be conducted as follows: placing the sample in a thermo-oxidative aging environment at 290° C. for 12 h to achieve aging, for example, placing the sample in a hot air drying oven to achieve aging. Because the aging is artificially accelerated, according to the tests in this way, if similar natural aging indexes are obtained once again in the future, it is easy to predict how long it will take for a silicone rubber composite insulator in a similar aging state to be replaced. Therefore, this method can accurately predict the future aging characteristics of the silicone rubber composite insulator.

Preferably, the subjecting the samples to a hardness test in step 3 may be conducted by a method the same as the method of the subjecting the samples to a hardness test in step 1 to obtain a Shore hardness value $Shore_{iwlh}$ of each sample, where i=A, B, C, or D; a hardness difference $Shore_{ilh}=Shore_{iwlh}-Shore_{iw}$ may be calculated for each sample after the thermo-oxidative aging; and an artificial accelerated evolution difference $\Delta H_{lh}=\Sigma Shore_{ilh}/4$ in Shore hardness of the four samples may be calculated.

In the present disclosure, methods for testing the hardness of the samples are basically similar, but after the hardness difference is calculated in step 3, a difference with the data before the thermo-oxidative aging can be calculated, such as to obtain an artificial accelerated evolution.

Step 3: The samples are subjected to thermo-oxidative aging; and after the thermo-oxidative aging is completed, the samples are subjected to a hardness test of artificial accelerated evolution, and position coordinates ($F_1$, $F_2$) of the samples in an aging space are calculated.

Preferably, in a laboratory evaluation process, the position coordinates ($F_1$, $F_2$) of the samples in the aging space may be calculated according to the following formula:

$F_1=-0.075\Delta H_{lh}+0.088\Delta CAV-0.201\Delta H_{shore}+0.246\Delta L-0.062\Delta IR-10.230$ $F_2=-0.006\Delta H_{lh}+0.169\Delta CAV-0.047\Delta H_{shore}+0.154\Delta L-0.096\Delta IR-21.269.$ In a first method of the present disclosure, multiple test indexes, such as an artificial accelerated evolution difference $\Delta H_{lh}$ in Shore hardness, an average static contact angle $\Delta CAV$, a natural evolution difference $\Delta H_{shore}$ in Shore hardness, a natural evolution difference $\Delta L$ in lightness, and a natural evolution $\Delta IR$ of absorbance rise rates, can be used for comprehensive calculation, and different coefficients are set according to an association strength between each index and the aging degree, such as to obtain the final position coordinates. In the present disclosure, coefficients in $F_1$ and $F_2$ expressions are obtained through a projection idea in FDA. Specifically, the FDA is a newly-developed dimensionality reduction technology, which can project high-latitude historical data into a low-dimensional data space by appropriately selecting a projection axis, and use low-dimensional representative information as characteristic information of historical data. In a dimensionality reduction process, this method can comprehensively consider various types of data such as Shore hardness, lightness, absorbance, and average static contact angle and can also consider the internal connection among various types of data, which is very suitable for the aging degree calculation in the present disclosure.

In the method for evaluating an aging state of a silicone rubber composite insulator according to an embodiment of the present disclosure, a calculation process is as follows: a calculation formula of position coordinates and centroid coordinates of various aging states are obtained through projection calculation with a large number of known samples in advance; and various performance measurement values of an unknown sample are obtained in steps 1 to 3 and substituted into the calculation formula to obtain position coordinates of the sample, a distance between the position coordinates of the sample and a centroid of each aging state is calculated, and an aging state of a centroid corresponding to the minimum value is an aging state of the sample.

In an embodiment of the present disclosure, 51 silicone rubber composite insulator umbrella skirts with known aging states are selected and numbered 1 to 51. According to aging states of the umbrella skirts, the 51 umbrella skirts are divided into three populations, including an unaging population $M_{unaging}$, a slightly-aging population $M_{slightly-aging}$, and a severely-aging population $M_{severely-aging}$, where the number of samples in each population is $n_{unaging}$, $n_{slightly-aging}$, and $n_{severely-aging}$, respectively. Each population can be represented as a combined vector of different parameters in multiple samples. For example, the unaging population $M_{unaging}$ can be expressed as a vector composed of various parameters $\Delta H_{lh}$, $\Delta CAV$, $\Delta H_{shore}$, $\Delta L$, and $\Delta IR$ and a constant 1 of all samples $m_{iunaging}$ in the population, where a value of i in the samples $m_{iunaging}$ is any natural number in $n_{unaging}$. In the present disclosure, the constant can be set to 1 first, and a value of a coefficient thereof can be calculated through subsequent steps.

After the above expression is realized, an average of each population can be calculated, for example, $$\mu_{unaging} = \frac{\sum m_{iunaging}}{n_{unaging}}.$$

According to the average of each population, an average of all samples can be calculated. A similar method is used to calculate an intra-population SS $S_{intra-population}$ of multiple samples within each population, and then calculate an average intra-population SS $S_{average\ intra-population} = S_{unaging} + S_{slightly-aging} + S_{severely-aging}$ of multiple populations. Finally, an inter-population SS $S_{inter-population}$ of multiple populations is calculated, which is obtained by summing squares between an average value of each population and a comprehensive average value of all populations.

After the calculation is completed, when a projection direction is assumed as a matrix $C = (C_{F1} > C_{F2})$, the intra-population SS after projection is $E_{aging\ state} = C^T \cdot S_{average\ intra-population} \cdot C$ and the inter-population SS after projection is $D_{aging\ state} = C^T \cdot S_{inter-population} \cdot C$.

Preferably, a calculation process of the projection matrix C may include: step 3.1: subjecting a preset sample group to overall classification to divide the preset sample group into n populations; step 3.2: calculating an intra-population SS of all samples in each population, and calculating an inter-population SS of multiple populations; and step 3.3: calculating the matrix C using an objective function that makes the intra-population SS minimum and the inter-population SS maximum after projection.

According to the FDA, a value of the matrix C is calculated using an objective function that makes the intra-population SS minimum and the inter-population SS maximum after projection. When the unique value of the projection matrix is determined, the calculation formula of the position coordinates in the aging space in the present disclosure can be determined. Specifically, since the matrix is obtained by multiplying and summing each item of data for the sample, a value of each item in the matrix C can be used as a coefficient for the position coordinate formula. Preferably, in an on-site evaluation process, the position coordinates of the samples in the aging space may be calculated only based on the natural evolution difference in lightness $\Delta L$ and the flexing resistance index $C_{dz}$.

In an embodiment of the present disclosure, in an on-site evaluation process, the position coordinates of the samples in the aging space may be calculated according to the following formula:

$F'_1 = 0.293\Delta L^* - 0.454 C_{dz} - 0.466$ $F'_2 = -0.002\Delta L + 1.159 C_{dz} - 0.814.$ In the present disclosure, in order to simplify the above-mentioned test and evaluation processes and the devices used in the evaluation, only two basic indexes can be adopted (namely, the color difference index and the flexing resistance index that are easily available on site) for the simple evaluation of the aging state of the material, and the FDA described above in the present disclosure is also used for solving (but the projection matrix is simplified) to obtain the above calculation formula. This kind of evaluation is very time-saving and labor-saving. Therefore, on-site evaluation can be used as a supplement to laboratory evaluation, which can improve the timeliness of the method when the accuracy requirements are not too high.

It should be noted that, in the present disclosure, it is not necessary to use data obtained by the test methods described above to calculate the position coordinates in the aging space. In addition to the content described above, the present disclosure can also use parameters such as a rise rate of an infrared absorption peak ratio, a difference in the relative area ratio of siloxane diffraction peak, a ratio of the content ratio of silicon to carbon, a ratio of the content ratio of oxygen to silicon, a difference in the average number of oxygen atoms, activation energy at different reaction depths between inner samples and outer samples to calculate the position coordinates in the aging space.

A method of parameter selection can be based on Wilk's lambda, which is obtained by multivariate analysis of variance (MANOVA). The method can be used to test the significance of each parameter, and when a significant difference is detected, the parameter can be used as a parameter required by the method of the present disclosure.

Step 4: The samples are classified in advance and an aging state centroid of each classified population is solved, a minimum aging distance is calculated based on the position coordinates in step 3, and the aging state of the silicone rubber composite insulator is evaluated based on the minimum aging distance.

Preferably, an aging state centroid of samples in each classified population may be calculated, a distance between each preset centroid and the position coordinates $(F_1, F_2)$ may be calculated, and a minimum distance value may be adopted as the minimum aging distance minL; and multiple classified populations may be determined, and when a discrimination index between any two classified populations is less than a set threshold, the number of classified populations may be reduced and then the aging state centroid may be recalculated.

Generally, the method of the present disclosure can divide the samples in advance by reasonably setting the number of classified populations in the sample group, and positions of multiple centroids can be solved in advance. However, sometimes after the sample group is divided according to the preset number of classified populations, it will be found that the number of classified populations is too large in a test process. In this case, the number of populations can be reduced, and consequently the dimensionality of the position coordinates in the sample space can be reduced. In this way, a simplified projection matrix can be obtained.

Preferably, the number of classified populations of samples may be 3, and an unaging state centroid ($F_{1\ unaging}$, $F_{2\ unaging}$), a slightly-aging state centroid ($F_{1\ slightly-aging}$, $F_{2\ slightly-aging}$), and a severely-aging state centroid ($F_{1\ severely-aging}$, $F_{2\ severely-aging}$) of the samples may be calculated; and in a laboratory evaluation process, distances of the unaging state centroid, the slightly-aging state centroid, and the severely-aging state centroid to the coordinate position may be each calculated.

In the present disclosure, a centroid refers to average values of coordinates of all samples in the aging state preset in advance in the aging space, which is obtained based on a large amount of aging test data. For example, according to the content in the embodiments of the present disclosure, centroid coordinates (average $F_{1\ aging\ state}$, average $F_{2\ aging\ state}$) can be obtained according to average values of each population of different populations into which 51 samples are divided. For example, coordinates of the unaging state centroid may be (average $F_{1\ unaging}$, average $F_{2\ unaging}$).

Distances of the three aging centroids to the position coordinates of the test sample are each calculated, and a state of the centroid corresponding to the shortest distance is the aging state of the test sample. In the present disclosure, each of the 51 samples is used as a test sample once again for verification, and the accuracy is as high as 93.5%. In an embodiment of the present disclosure, centroid coordinates of each aging state are shown in Table 1; and according to position coordinates of each aging centroid in Table 1, a distance of the centroid to the position coordinates of the sample is calculated to obtain three different aging distances. Finally, a minimum distance is selected from the three different aging distances to serve as the minimum aging distance minL.

TABLE 1

Centroid coordinates of each aging state

|  | F1 | F2 |
| --- | --- | --- |
| Unaging | −1.027 | −0.528 |
| Slightly-aging | −2.418 | 1.622 |
| Severely-aging | 3.559 | 0.268 |

Distances between the position coordinates and the centroids can be calculated by the Euclidean distance formula to obtain the minimum distance between the position coordinates and the centroids in a two-dimensional (2D)) space.

Figure 2:
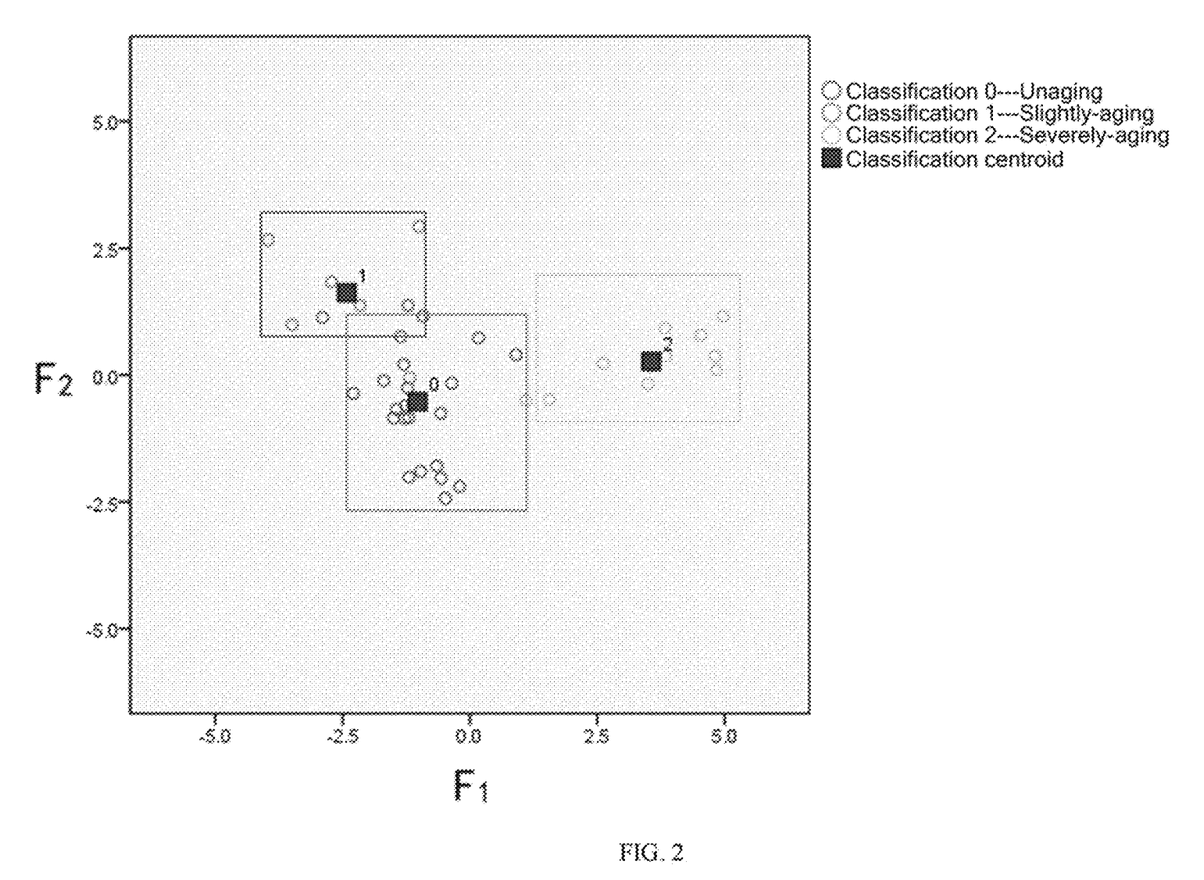
FIG. 2 is a schematic diagram of a method for evaluating according to sample position coordinates and a preset centroid in a first embodiment of the method for evaluating an aging state of a silicone rubber composite insulator according to the present disclosure.

FIG. 2 is a schematic diagram of a method for evaluating according to sample position coordinates and a preset centroid in a first embodiment of the method for evaluating an aging state of a silicone rubber composite insulator according to the present disclosure. As shown in FIG. 2, the calculation method in the present disclosure is used to mark the coordinate position of the sample on a 2D plane, the coordinate position is compared with the position of the preset centroid, and a distance between the two is calculated, such that sample coordinates on different planes can be obtained, which may be in an unaging, slightly-aging, or severely-aging range.

In a one-dimensional (1D) space, laboratory aging evaluation results of 51 test samples are shown in Table 2.

TABLE 2

Laboratory evaluation results of 51 samples

| No. | Classification result |
| --- | --- |
| 1 | Severely-aging |
| 2 | Severely-aging |
| 3 | Slightly-aging |
| 4 | Slightly-aging |
| 5 | Slightly-aging |
| 6 | Severely-aging |
| 7 | Slightly-aging |
| 8 | Slightly-aging |
| 9 | Slightly-aging |
| 10 | Slightly-aging |
| 11 | Unaging |
| 12 | Unaging |
| 13 | Unaging |
| 14 | Slightly-aging |
| 15 | Unaging |
| 16 | Unaging |
| 17 | Unaging |
| 18 | Unaging |
| 19 | Slightly-aging |
| 20 | Unaging |
| 21 | Unaging |
| 22 | Severely-aging |
| 23 | Severely-aging |
| 24 | Severely-aging |
| 25 | Unaging |
| 26 | Unaging |
| 27 | Unaging |
| 28 | Severely-aging |
| 29 | Severely-aging |
| 30 | Severely-aging |
| 31 | Slightly-aging |
| 32 | Severely-aging |
| 33 | Severely-aging |
| 34 | Severely-aging |
| 35 | Severely-aging |
| 36 | Severely-aging |
| 37 | Unaging |
| 38 | Unaging |
| 39 | Unaging |
| 40 | Unaging |
| 41 | Unaging |
| 42 | Slightly-aging |
| 43 | Unaging |
| 44 | Slightly-aging |
| 45 | Unaging |
| 46 | Unaging |
| 47 | Slightly-aging |
| 48 | Unaging |
| 49 | Unaging |
| 50 | Unaging |
| 51 | Unaging |

Figure 3:
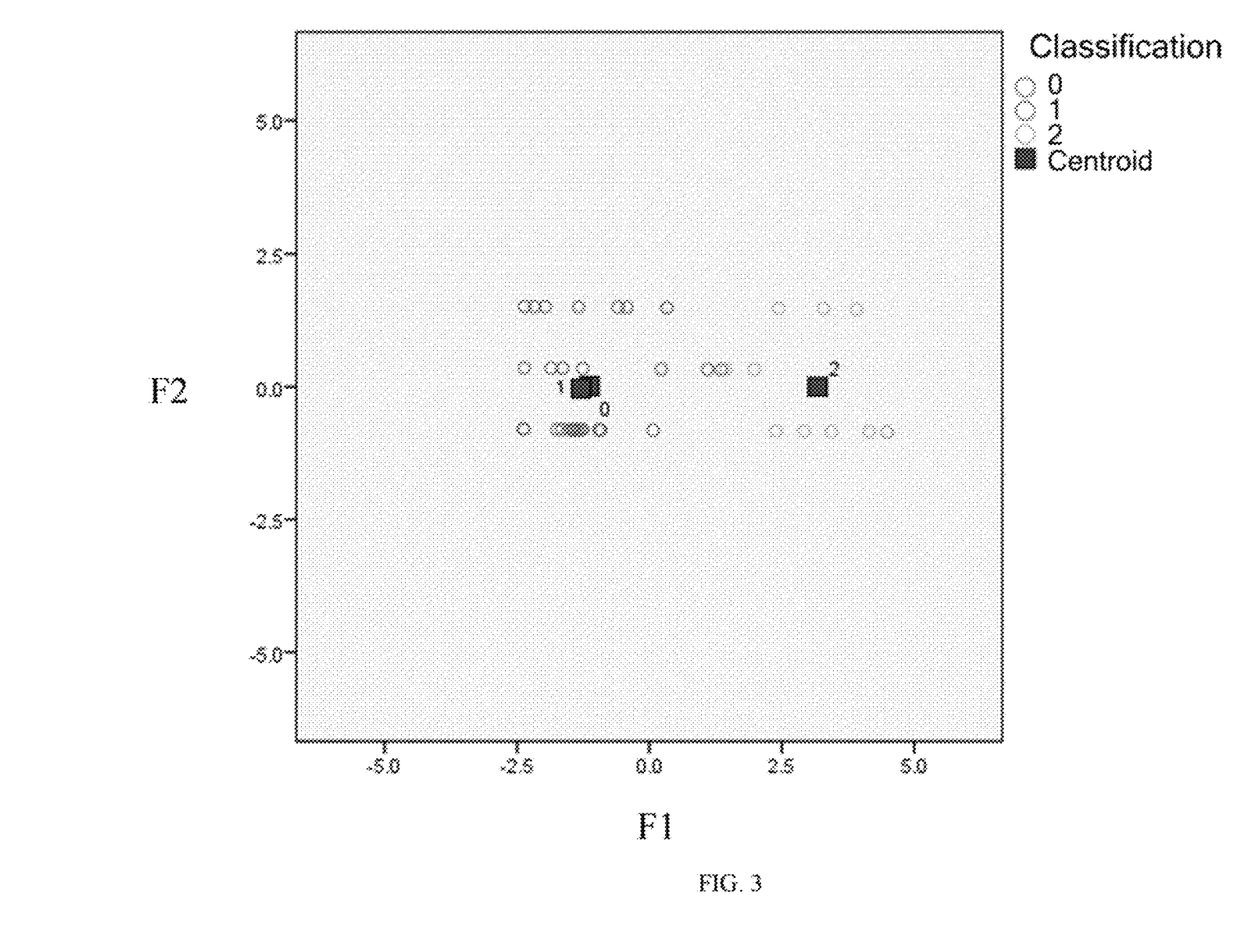
FIG. 3 is a schematic diagram of a method for evaluating according to sample position coordinates and a preset centroid in a second embodiment of the method for evaluating an aging state of a silicone rubber composite insulator according to the present disclosure.

Preferably, in an on-site evaluation process, populations may be simplified into non-aging populations and aging populations, and distances of a non-aging state centroid and an aging state centroid to the coordinate position may be each calculated.

FIG. 3 is a schematic diagram of a method for evaluating according to sample position coordinates and a preset centroid in a second embodiment of the method for evaluating an aging state of a silicone rubber composite insulator according to the present disclosure. The method in FIG. 3 can be obtained according to the second method of generating position coordinates in the present disclosure. With reference to this method, it can be found that, although this method still sets the two coordinate parameters $F_1$ and $F_2$ and coordinates of multiple samples also fall into the 2D plane, only the coordinate value $F_1$ mainly affects the aging degree of the sample in this method. The value of $F_2$ has little effect on determining the aging degree. Therefore, in an actual calculation process, the method can be further optimized, that is, only a distance between the value of $F_1$ and multiple different centroids is calculated.

After the optimization, it is found that the unaging centroid and the slightly-aging centroid are highly overlapped. Therefore, the 51 samples for on-site aging evaluation are reclassified, and only two different populations (aging and unaging) are obtained.

In the embodiment of the 51 samples in the present disclosure, the unaging centroid is −1.177, the aging centroid is 3.211, and $F_1''=0.293\Delta L^*-0.454C_{dz}-0.466$ is solved.

Figure 4:
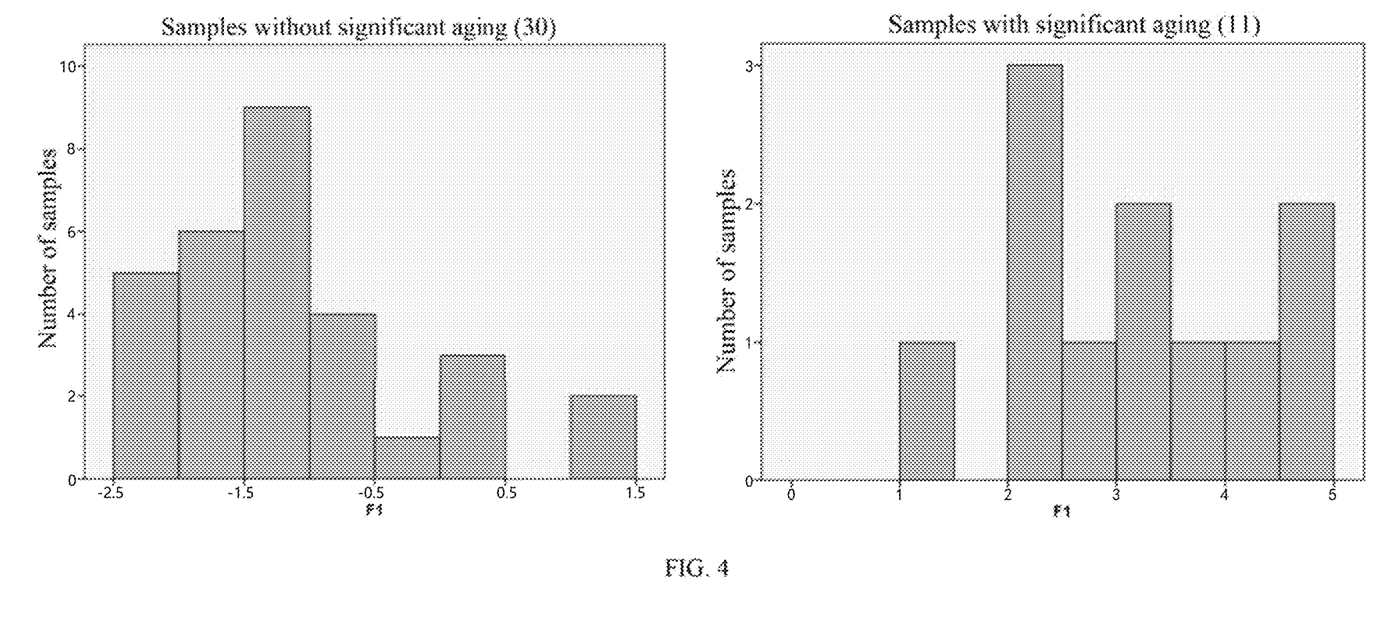
FIG. 4 is a schematic diagram illustrating the distribution of evaluation results of multiple groups of samples in the second embodiment of the method for evaluating an aging state of a silicone rubber composite insulator according to the present disclosure.

FIG. 4 is a schematic diagram illustrating the distribution of evaluation results of multiple groups of samples in the second embodiment of the method for evaluating an aging state of a silicone rubber composite insulator according to the present disclosure. In order to verify the accuracy of the method in the present disclosure, 51 groups of samples collected from 4 silicone rubber composite insulators are subjected to tests and state evaluation. Results show that there are 30 samples without significant aging (namely, samples classified in the unaging population), and there are 11 samples with significant aging (namely, samples classified in the aging population).

Figure 5:
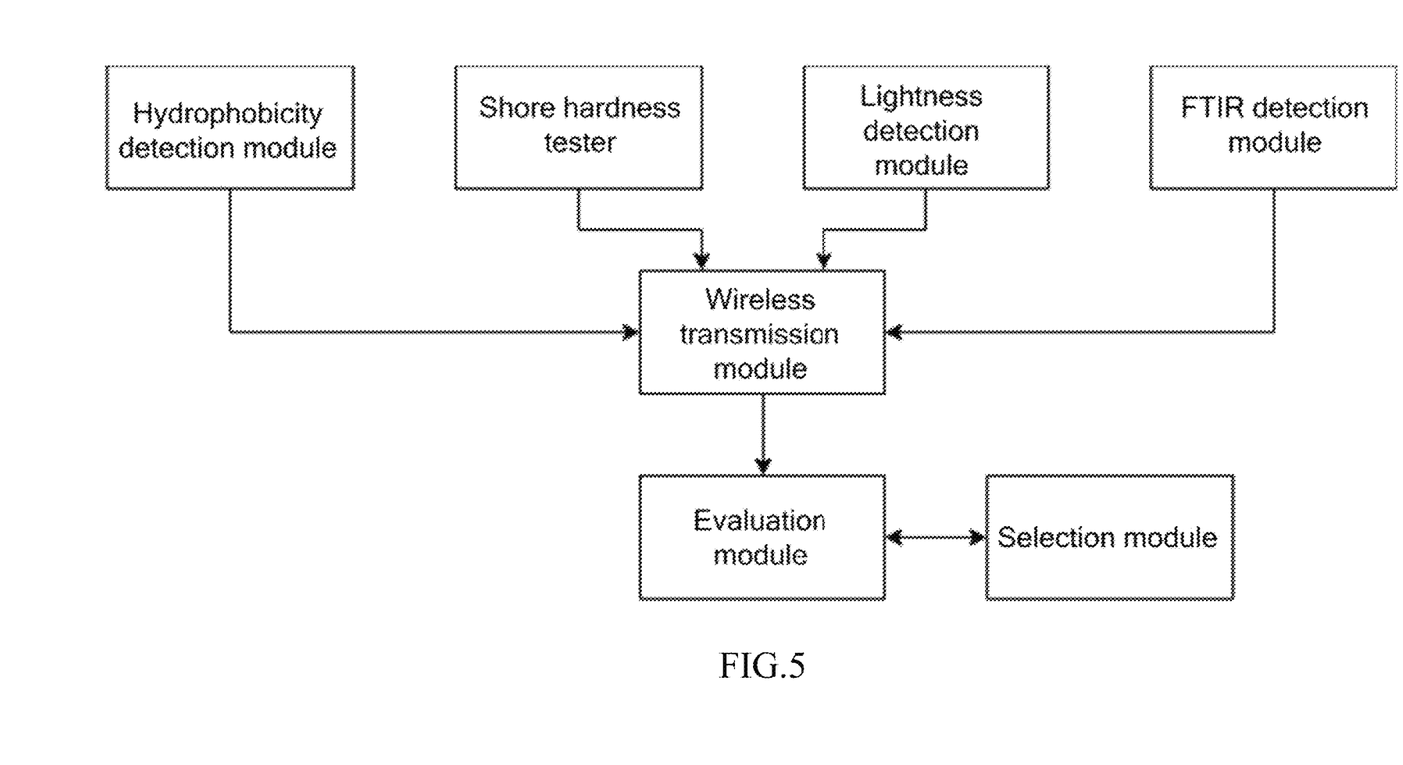
FIG. 5 is a block diagram of the device for evaluating an aging state of a silicone rubber composite insulator according to the present disclosure.

FIG. 5 is a block diagram of the device for evaluating an aging state of a silicone rubber composite insulator according to the present disclosure. As shown in FIG. 5, in a second aspect of the present disclosure, a device for evaluating an aging state of a silicone rubber composite insulator is provided, where the device integrates a hydrophobicity detection module, a Shore hardness tester, a lightness detection module, an FTIR detection module, a wireless transmission module, and an evaluation module, where the hydrophobicity detection module, the Shore hardness tester, the lightness detection module, and the FTIR detection module are configured to test samples by the method in the first aspect of the present disclosure; the wireless transmission module is configured to output test results of the hydrophobicity detection module, the Shore hardness tester, the lightness detection module, and the FTIR detection module to the evaluation module in real time; and the evaluation module is configured to evaluate the test results and display the aging state of the silicone rubber composite insulator.

Preferably, the device may further include a selection module configured to select a calculation method of position coordinates of the samples in an aging space.

In an embodiment of the present disclosure, the hydrophobicity detection module may be a complete set of hydrophobicity detection devices, which can measure an included angle (namely, the static contact angle) between water droplets on a surface of the silicone rubber material and the surface of the material by the liquid-dropping method. The lightness detection module can be a complete set of lightness detection devices, which can measure a lightness value L of the silicone rubber material under specific light in a color space L*a*b, and display the lightness value in the numerical form. The FTIR detection module can be an infrared spectrum detector, and has the accessory function of attenuated total reflectance (ATR), which can measure the absorbance of the silicone rubber material in an infrared wavelength range of 600 cm$^{-1}$ to 4,000 cm$^{-1}$ and can also achieve the peak height calibration. The wireless transmission module may be one or more processors with a communication interface that can implement a communication protocol; if necessary, the wireless transmission module may also include a memory and related interfaces, a system transmission bus, and the like, which have 4G, 5G, and other wireless transmission functions; and the processor can execute a program-related code to implement a corresponding function. The evaluation module may include one or more processors with a communication interface that can implement a communication protocol, a memory, related interfaces, a system transmission bus, a display, and the like; and the processor can execute a program-related code to implement a corresponding function. The selection module may be one or more processors with a communication interface that can implement a communication protocol, and the processor can execute a program-related code to implement a corresponding function. Or, an alternative solution is that the wireless transmission module, the evaluation module, and the selection module may share an integrated chip or share devices such as a processor, a memory, and a display. The shared processor or chip can execute a program-related code to implement a corresponding function.

The present disclosure has the following beneficial effects: Compared with the prior art, the method for evaluating an aging state of a silicone rubber composite insulator provided in the present disclosure can determine an overall aging state of the silicone rubber composite insulator by subjecting samples of the silicone rubber composite insulator to hydrophobicity, flexing resistance, hardness, color, and absorbance tests. In addition, in the present disclosure, the samples can be subjected to thermo-oxidative aging, and after the thermo-oxidative aging is completed, aging test results of the silicone rubber composite insulator are further determined, such that the future aging performance of the silicone rubber composite insulator product can be accurately predicted, and thus operation and maintenance personnel of a power grid can reasonably choose the time to replace the composite insulator product.

The implementation examples of the present disclosure are described in detail by the applicants of the present disclosure with reference to the accompanying drawings in the specification. However, those skilled in the art should understand that the above implementation examples are only preferred embodiments of the present disclosure, and the detailed description is only to help readers better understand the spirit of the present disclosure, rather than to limit the protection scope of the present disclosure. On the contrary, any improvement or modification based on the spirit of the present disclosure shall fall within the protection scope of the present disclosure.

The invention claimed is:

1. A method for evaluating an aging state of a silicone rubber composite insulator, comprising the following steps:
   step 1: collecting samples from the silicone rubber composite insulator, subjecting samples in a surface layer successively to hydrophobicity, flexing resistance, hardness, color, and absorbance tests, and subjecting samples in a center layer successively to hardness, color, and absorbance tests;
   step 2: determining an average static contact angle, a flexing resistance index, a hardness difference, a color difference, and an absorbance rise rate of the samples during a natural evolution process according to the tests in step 1;
   step 3: subjecting the samples to thermo-oxidative aging; and after the thermo-oxidative aging is completed, subjecting the samples to a hardness test of artificial accelerated evolution, and calculating position coordinates ($F_1$, $F_2$) of the samples in an aging space; and
   step 4: classifying the samples in advance and solving an aging state centroid of each classified population, calculating a minimum aging distance based on the position coordinates in step 3, and evaluating the aging state of the silicone rubber composite insulator based on the minimum aging distance.

2. The method for evaluating an aging state of a silicone rubber composite insulator according to claim 1, wherein
   the step of collecting samples from the silicone rubber composite insulator comprises:
   step 1.1: randomly collecting a whole umbrella skirt $S_{zp}$ of a second umbrella or a third umbrella of a high-voltage end from the silicone rubber composite insulator;

step 1.2: collecting samples $A_w$, $B_w$, $C_w$, and $D_w$ respectively from four positions a, b, c, and d on an upper surface of the whole umbrella skirt $S_{zp}$; and step 1.3: collecting samples $A_n$, $B_n$, $C_n$, and $D_n$ respectively from four positions a, b, c, and d in a split layer of the whole umbrella skirt $S_{zp}$;

wherein a connecting line ab is perpendicular to a connecting line cd, and an intersection point of the two is located at a pivot of the whole umbrella skirt; and distances of the four points a, b, c, and d to the pivot of the whole umbrella skirt are equal.

3. The method for evaluating an aging state of a silicone rubber composite insulator according to claim 2, wherein
the samples $A_w$, $B_w$, $C_w$, and $D_w$ are each subjected to a hydrophobicity test, and static contact angles of surfaces of the samples are recorded as $CAV_{A_w}$, $CAV_{B_w}$, $CAV_{C_w}$, and $CAV_{D_w}$; and an average static contact angle $\Delta CAV = \Sigma CAV_{i_w}/4$ of the samples is calculated based on the static contact angles of the surfaces of the samples, wherein i=A, B, C, or D.

4. The method for evaluating an aging state of a silicone rubber composite insulator according to claim 3, wherein
the subjecting the samples to a flexing resistance test specifically comprises: folding an edge of the sample $S_{zp}$ at 180°, and determining a flexing resistance index $C_{dz}$ based on a crack state at a crease position;
wherein $$C_{dz} = \begin{cases} 0, & \text{There are cracks} \geq 2 \text{ mm} \\ 1, & \text{There are cracks} \leq 2 \text{ mm} \\ 2, & \text{There is no crack} \end{cases}$$

5. The method for evaluating an aging state of a silicone rubber composite insulator according to claim 4, wherein
the subjecting the samples to a hardness test in step 1 further comprises:
subjecting the samples $A_w$, $B_w$, $C_w$, $D_w$, $A_n$, $B_n$, $C_n$, and $D_n$ to a Shore hardness test to obtain Shore hardness values $Shore_{iw}$ and $Shore_{in}$ of a sample at each position, wherein i=A, B, C, or D;
calculating a Shore hardness difference $Shore_i = Shore_{iw} - Shore_{in}$ of a sample at each position; and
calculating a natural evolution difference $\Delta H_{shore} = \Sigma (Shore_{iw} - Shore_{in})/4$ in Shore hardness of the samples at the four positions.

6. The method for evaluating an aging state of a silicone rubber composite insulator according to claim 5, wherein
the subjecting the samples to a color test in step 1 further comprises:
subjecting the samples $A_w$, $B_w$, $C_w$, $D_w$, $A_n$, $B_n$, $C_n$, and $D_n$ to a lightness test to obtain lightness values $L_{iw}$ and $L_{in}$ of a sample at each position in a color space L*a*b, wherein i=A, B, C, or D;
calculating a lightness difference $L_i = L_{iw} - L_{in}$ of a sample at each position; and
calculating a natural evolution difference $\Delta L = \Sigma (L_{iw} - L_{in})/4$ in lightness of the samples at the four positions.

7. The method for evaluating an aging state of a silicone rubber composite insulator according to claim 6, wherein
the samples $A_w$, $B_w$, $C_w$, $D_w$, $A_n$, $B_n$, $C_n$, and $D_n$ are subjected to an absorbance test, and absorbance ratios $R_{iw}$ and $R_{in}$ of a sample at each position are recorded, wherein i=A, B, C, or D;

an absorbance rise rate $$IR_i = \frac{(R_{iw} - R_{in})}{R_{in}} * 100\%$$

of a sample at each position is calculated; and
a natural evolution $\Delta IR = \Sigma IR_i/4$ of the absorbance rise rates of the samples at the four positions is calculated.

8. The method for evaluating an aging state of a silicone rubber composite insulator according to claim 7, wherein
the absorbance ratios $R_{iw}$ and $R_{in}$ of the sample at each position are determined as follows:
determining an absorbance peak of the sample at a wavelength corresponding to siloxy and an absorbance peak at a wavelength corresponding to silyl; and
calculating a ratio of the two peaks to obtain the absorbance ratios $R_{iw}$ and $R_{in}$.

9. The method for evaluating an aging state of a silicone rubber composite insulator according to claim 8, wherein
a method of the thermo-oxidative aging in step 3 comprises: subjecting the samples $A_w$, $B_w$, $C_w$, and $D_w$ simultaneously to thermo-oxidative aging at 290° C. for 12 h.

10. The method for evaluating an aging state of a silicone rubber composite insulator according to claim 9, wherein
the subjecting the samples to a hardness test in step 3 is conducted by a method the same as the method of the subjecting the samples to a hardness test in step 1 to obtain a Shore hardness value $Shore_{iwlh}$ of each sample, wherein i=A, B, C, or D;
a hardness difference $Shore_{ilh} = Shore_{iwlh} - Shore_{iw}$ is calculated for each sample after the thermo-oxidative aging; and
an artificial accelerated evolution difference $\Delta H_{lh} = \Sigma Shore_{ilh}/4$ in Shore hardness of the four samples is calculated.

11. The method for evaluating an aging state of a silicone rubber composite insulator according to claim 10, wherein
in a laboratory evaluation process, the position coordinates $(F_1, F_2)$ of the samples in the aging space are calculated according to the following formula:

$F_1 = \alpha_1 \Delta H_{lh} + \alpha_2 \Delta CAV + \alpha_3 \Delta H_{shore} + \alpha_4 \Delta L + \alpha_5 \Delta IR + \alpha_6$ $F_2 = \beta_1 \Delta H_{lh} + \beta_2 \Delta CAV + \beta_3 \Delta H_{shore} + \beta_4 \Delta L + \beta_5 \Delta IR + \beta_6$, wherein a projection matrix $$C = \begin{bmatrix} \alpha_1 & \alpha_2 & \alpha_3 & \alpha_4 & \alpha_5 & \alpha_6 \\ \beta_1 & \beta_2 & \beta_3 & \beta_4 & \beta_5 & \beta_6 \end{bmatrix}$$

composed of coefficients in the position coordinate calculation formula is calculated in advance based on Fisher discriminant analysis (FDA).

12. The method for evaluating an aging state of a silicone rubber composite insulator according to claim 11, wherein
a calculation process of the projection matrix C comprises:
step 3.1: subjecting a preset sample group to overall classification to divide the preset sample group into n populations according to an aging degree;
step 3.2: calculating an intra-population sum of squares (SS) of all samples in each population, and calculating an inter-population SS of multiple populations; and
step 3.3: calculating the matrix C using an objective function that makes the intra-population SS minimum and the inter-population SS maximum after projection.

13. The method for evaluating an aging state of a silicone rubber composite insulator according to claim 12, wherein
in an on-site evaluation process, the position coordinates of the samples in the aging space are calculated only based on the natural evolution difference in lightness $\Delta L$ and the flexing resistance index $C_{dz}$.

14. The method for evaluating an aging state of a silicone rubber composite insulator according to claim 12, wherein
an aging state centroid of samples in each classified population is calculated, a distance between each preset centroid and the position coordinates $(F_1, F_2)$ is calculated, and a minimum distance value is adopted as the minimum aging distance minL; and multiple classified populations are determined, and when a discrimination index between any two classified populations is less than a set threshold, the number of classified populations is reduced and then the aging state centroid is recalculated.

15. The method for evaluating an aging state of a silicone rubber composite insulator according to claim 14, wherein
the number of classified populations of samples is 3, and an unaging state centroid ($F_{1\ unaging}$, $F_{2\ unaging}$), a slightly-aging state centroid ($F_{1\ slightly-aging}$, $F_{2\ slightly-aging}$), and a severely-aging state centroid ($F_{1\ severely-aging}$, $F_{2\ severely-aging}$) of the samples are calculated; and in a laboratory evaluation process, distances of the unaging state centroid, the slightly-aging state centroid, and the severely-aging state centroid to the coordinate position are each calculated.

16. The method for evaluating an aging state of a silicone rubber composite insulator according to claim 15, wherein
in an on-site evaluation process, populations are divided into non-aging populations and aging populations, and distances of a non-aging state centroid and an aging state centroid to the coordinate position are each calculated.

17. A device for evaluating an aging state of a silicone rubber composite insulator, wherein
the device integrates a hydrophobicity detection module, a Shore hardness tester, a lightness detection module, a Fourier transform infrared spectroscopy (FTIR) detection module, a wireless transmission module, and an evaluation module, wherein the hydrophobicity detection module, the Shore hardness tester, the lightness detection module, and the FTIR detection module are configured to test samples by the method according to claim 1;

the wireless transmission module is configured to output test results of the hydrophobicity detection module, the Shore hardness tester, the lightness detection module, and the FTIR detection module to the evaluation module in real time; and the evaluation module is configured to evaluate the test results and display the aging state of the silicone rubber composite insulator.

18. The device for evaluating an aging state of a silicone rubber composite insulator according to claim 17, wherein
the device further comprises a selection module configured to select a calculation method of position coordinates of the samples in an aging space.

* * * * *